United States Patent
Xu et al.

(10) Patent No.: US 10,501,511 B2
(45) Date of Patent: Dec. 10, 2019

(54) LOW MOLECULAR POLYPEPTIDE FOR PREVENTING AND TREATING INFLAMMATION AND USE THEREOF

(71) Applicant: SHANGHAI FIRST PEOPLE'S HOSPITAL, Shanghai (CN)

(72) Inventors: Xun Xu, Shanghai (CN); Lili Wang, Shanghai (CN); Yi Xu, Shanghai (CN)

(73) Assignee: SHANGHAI FIRST PEOPLE'S HOSPITAL, Shanghai (CN)

( * ) Notice: Subject to any disclaimer, the term of this patent is extended or adjusted under 35 U.S.C. 154(b) by 0 days.

(21) Appl. No.: 15/024,229

(22) PCT Filed: Aug. 13, 2014

(86) PCT No.: PCT/CN2014/084293
§ 371 (c)(1),
(2) Date: Mar. 24, 2016

(87) PCT Pub. No.: WO2015/021924
PCT Pub. Date: Feb. 19, 2015

(65) Prior Publication Data
US 2017/0037099 A1    Feb. 9, 2017

(30) Foreign Application Priority Data
Aug. 15, 2013    (CN) .......................... 2013 1 0357596

(51) Int. Cl.
C07K 14/475    (2006.01)
A61K 38/00    (2006.01)
A61K 9/00    (2006.01)

(52) U.S. Cl.
CPC ........ *C07K 14/4753* (2013.01); *A61K 9/0014* (2013.01); *A61K 9/0019* (2013.01); *A61K 9/0048* (2013.01); *A61K 38/00* (2013.01)

(58) Field of Classification Search
None
See application file for complete search history.

(56) References Cited

U.S. PATENT DOCUMENTS

2003/0148950 A1    8/2003    Xin et al.
2013/0331545 A1*   12/2013   Melnyk .................. C07K 1/026
530/339

FOREIGN PATENT DOCUMENTS

CN    102827253        12/2012
FR    2971509     *    2/2011

OTHER PUBLICATIONS

Xu. Y. et al. (A novel antiangiogenic peptide derived from hepatocyte growth factor inhibits neovascularization in vitro and in vivo. Molecular Vision. Oct. 7, 2010 (Oct. 7, 2010), vol. 16, No. 214, pp. 1982-1995).*
Sun, Y. et al. (H-RN, a peptide derived from hepatocyte growth factor, corneal neovascularization by inducing endothelialapoptosis and arresting the cell cycle. BMC Cell Biology. Feb. 24, 2013 (Feb. 24, 2013), vol. 14, document No. 8).*
Imhof et al. "Angiogenesis and inflammation face off." Nature Medicine 12, 171-172 (2006) https://www.nature.com/articles/nm0206-171.*
Chan et al. (2006). Ocular Inflammation and Neovascularization. In: Tombrain-Tink J., Barnstable C.J. (eds) Ocular Angiogenesis. Opthalmology Research. Humana Press. Available online: https://link.springer.com/content/pdf/10.1007%2F978-1-59745-047-8.pdf.*
International Search Report for international application No. PCT/CN2014/084293, dated Oct. 14, 2014 (8 pages, including English translation).
Y. Sun et al., "H-RN, a peptide derived from hepatocyte growth factor, inhibits corneal neovascularization by inducing endothelial apoptosis and arresting the cell cycle," BMC Cell Biology (2013), vol. 14, No. 8, 10 pages.
Y. Xu et al., "A novel antiangiogenic peptide derived from hepatocyte growth factor inhibits neovascularization in vitro and in vivo," Molecular Vision (2010), vol. 16, p. 1982-1995.

* cited by examiner

*Primary Examiner* — Maury A Audet
(74) *Attorney, Agent, or Firm* — Hamre, Schumann, Mueller & Larson, P.C.

(57) ABSTRACT

Disclosed are a low molecular polypeptide for preventing and treating inflammation, a preparation method and the use thereof and a pharmaceutical composition containing the polypeptide, wherein the polypeptide can penetrate the eye tissue barrier, can maintain a high concentration in neutral tears, aqueous humour and vitreous humour, and can be used to treat inflammation.

5 Claims, 3 Drawing Sheets
Specification includes a Sequence Listing.

```
                          SEQUENCE LISTING

<160> NUMBER OF SEQ ID NOS: 9

<210> SEQ ID NO 1
<211> LENGTH: 33
<212> TYPE: DNA
<213> ORGANISM: artificial sequence
<220> FEATURE:
<223> OTHER INFORMATION: CDS
<220> FEATURE:
<221> NAME/KEY: CDS
<222> LOCATION: (1)..(33)

<400> SEQUENCE: 1 cga aat cct cga ggg gaa gaa ggg gga ccc tgg                          33

<210> SEQ ID NO 2
<211> LENGTH: 11
<212> TYPE: PRT
<213> ORGANISM: artificial sequence
<220> FEATURE:
<223> OTHER INFORMATION: Polypeptide

<400> SEQUENCE: 2

Arg Asn Pro Arg Gly Glu Glu Gly Gly Pro Trp
1               5                   10

<210> SEQ ID NO 3
<211> LENGTH: 11
<212> TYPE: PRT
<213> ORGANISM: artificial sequence
<220> FEATURE:
<223> OTHER INFORMATION: Polypeptide

<400> SEQUENCE: 3

Arg Asn Pro Lys Gly Glu Glu Gly Gly Pro Trp
1               5                   10

<210> SEQ ID NO 4
<211> LENGTH: 11
<212> TYPE: PRT
<213> ORGANISM: artificial sequence
<220> FEATURE:
<223> OTHER INFORMATION: Polypeptide

<400> SEQUENCE: 4

Lys Gln Pro Arg Gly Glu Glu Gly Gly Pro Trp
1               5                   10

<210> SEQ ID NO 5
<211> LENGTH: 11
<212> TYPE: PRT
<213> ORGANISM: artificial sequence
<220> FEATURE:
<223> OTHER INFORMATION: Polypeptide

<400> SEQUENCE: 5

Arg Asn Pro Arg Pro Glu Glu Gly Gly Ala Tyr
1               5                   10

<210> SEQ ID NO 6
<211> LENGTH: 11
```

```
<212> TYPE: PRT
<213> ORGANISM: artificial sequence
<220> FEATURE:
<223> OTHER INFORMATION: Polypeptide

<400> SEQUENCE: 6

Gln Asn Pro Arg Gly Asp Glu Pro Gly Pro Trp
1               5                   10

<210> SEQ ID NO 7
<211> LENGTH: 9
<212> TYPE: PRT
<213> ORGANISM: artificial sequence
<220> FEATURE:
<223> OTHER INFORMATION: Polypeptide

<400> SEQUENCE: 7

Asn Pro Arg Gly Glu Glu Gly Gly Pro
1               5

<210> SEQ ID NO 8
<211> LENGTH: 13
<212> TYPE: PRT
<213> ORGANISM: artificial sequence
<220> FEATURE:
<223> OTHER INFORMATION: Polypeptide

<400> SEQUENCE: 8

Arg Asn Pro Arg Gly Glu Glu Gly Gly Pro Trp Cys Phe
1               5                   10

<210> SEQ ID NO 9
<211> LENGTH: 11
<212> TYPE: PRT
<213> ORGANISM: artificial sequence
<220> FEATURE:
<223> OTHER INFORMATION: Polypeptide

<400> SEQUENCE: 9

Gly Pro Glu Arg Trp Arg Gly Pro Asn Gly Glu
1               5                   10
```

LOW MOLECULAR POLYPEPTIDE FOR PREVENTING AND TREATING INFLAMMATION AND USE THEREOF

TECHNICAL FIELD

The present invention relates to the bio-pharmaceutical field. Specifically, the present invention related to a new type of small molecule polypeptide, which is called H-RN, for preventing and treating inflammatory diseases. The present invention further relates to a preparation method and use of said polypeptide, and a pharmaceutical composition comprising the polypeptide.

BACKGROUND

Eye uveitis is a kind of immunogenicity disease which is intractable and common in clinical. The disease can damage the blood-ocular barrier, and cause hyperplasia of adjacent tissues within the eyes, thereby inducing cataracts, macular edema, secondary glaucoma, and finally ocular tissue damage. The disease is of high blinding-rate, seriously affect the visual quality and life quality of patients. In western countries, about 35% of uveitis patients exhibit varying degrees of visual impairment. The blinding-rate of domestic uveitis patients is 18.76%.

Currently, the treatment of uveitis mainly is local or systemic use of non-steroidal anti-inflammatory drugs, hormones and immunosuppressive agents. However, hormones or immunosuppressive agents inevitably induce some serious side effects, such as cataracts, glaucoma, infections, and renal toxicity; while non-steroidal anti-inflammatory drugs have strong local irritation, and large molecular weight, therefore, the local effective concentration of drug in the eye tissue is, to some extent, limited due to the low permeability of the eye barrier. In addition, drug screening or symptomatic treatment against a variety of pathological results caused by uveitis such as angiogenesis, hyperblastosis and the like can often only relatively alleviate the symptoms, but can not effectively suppress the primary lesion of uveitis, i.e. sthenic inflammatory reaction.

In recent years, an increasing number of biological agents have been proved in laboratory or clinically to have activity of inhibiting ocular inflammation, including antioxidants (e.g. benfotiamine, N-acetylcysteine, etc.), plant extracts, anti-cytokine monoclonal antibody (such as Daclizumab, a monoclonal anti-IL-2 receptor α subunit antibody, Infliximab, a monoclonal anti-TNF-α antibody) and the like. However, these biological agents have many deficiencies, such as large molecular weight, complex in vitro synthesis, complicated recombinant expression and purification processes during the preparation and endotoxin residue. And the biological activity is prone to be inactivated due to the protein conformational changes and modifications And there are risks of serious complications, such as tissue damage because it has large molecular weight, it is difficult to pass through the blood-ocular barrier, and repeated intravitreal injections or transgenic methods are needed to play the role of anti-inflammation.

When developing effective inhibitors of ocular inflammation, the particularity of the ocular drugs should be sufficiently considered.

Firstly, there are many anatomical and functional barriers in eyes. Systemic administration usually cannot result in a local sufficient concentration of drug in ocular tissue due to the blood-aqueous humor barrier and blood-retina barrier. Theoretically, in topical administration, such as injection in vitreous cavity, it is difficult for any macromolecule larger than 76.5 kDa to penetrate the retina and act on the retinal and choroidal vessel.

Secondly, the solubility of the drugs in the hydrophilic tears, aqueous humor, and vitreous humor is positively correlated to their effects.

Thirdly, for the above major reasons, the bioavailability of ocular drugs is very low. To improve it, the administration concentration of drugs should be increased. However, high concentrations of drugs exhibit significant toxicity, so that high dose cannot be used in either systemic or topical administration.

Fourthly, currently a series of relatively safe endogenous inhibitors for inflammation have been demonstrated. However, due to their relative large molecular weight and complicated spatial conformation, these inhibitors have disadvantages in preparation such as complicated recombinant expression and purification processes, residual endotoxin and so on.

Compared with a variety of currently studied protein inhibitors for inflammation, polypeptide inhibitors for inflammation have many outstanding advantages such as simple synthetic method, readiness to be chemically modified, low immunogenicity, high solubility, high bioavailability, strong tissue penetration, various administration route, low cost and so on.

Therefore, there is an urgent need to develop a small molecule anti-inflammation agent which is safe, effective, and suitable for eye ball tissues.

SUMMARY OF INVENTION

The object of the invention is to provide a small molecule polypeptide H-RN and fragments, analogues and derivatives thereof, which are safe, effective and suitable for eye ball tissue for inhibiting inflammation.

Another object of the present invention is to provide preparation methods and uses of said polypeptides.

In the first aspect, the present invention provides a polypeptide of Formula I, or a pharmaceutically acceptable salt thereof.

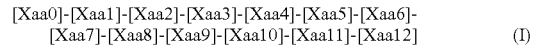

[Xaa0]-[Xaa1]-[Xaa2]-[Xaa3]-[Xaa4]-[Xaa5]-[Xaa6]-[Xaa7]-[Xaa8]-[Xaa9]-[Xaa10]-[Xaa11]-[Xaa12]  (I)

wherein,

Xaa0 is absent, or a peptide segment consisting of 1-3 amino acids;

Xaa1 is an amino acid selected from the group consisting of Arg, Lys and Gln;

Xaa2 is an amino acid selected from the group consisting of Asn and Gln;

Xaa3 is an amino acid selected from the group consisting of Pro and Ala;

Xaa4 is an amino acid selected from the group consisting of Arg and Lys;

Xaa5 is an amino acid selected from the group consisting of Gly and Ala;

Xaa6 is an amino acid selected from the group consisting of Glu and Asp;

Xaa7 is an amino acid selected from the group consisting of Glu and Asp;

Xaa8 is an amino acid selected from the group consisting of Gly and Ala;

Xaa9 is an amino acid selected from the group consisting of Gly and Ala;

Xaa10 is an amino acid selected from the group consisting of Pro and Ala;

Xaa11 is an amino acid selected from the group consisting of Trp, Tyr and Phe;

Xaa12 is absent, or a peptide segment consisting of 1-3 amino acids; and the polypeptide exhibits an activity of inhibiting inflammation.

In another preferred embodiment, Xaa0 and Xaa12 are absent.

In another preferred embodiment, Xaa1 is Arg, Xaa4 is Arg, Xaa10 is Pro, and Xaa11 is Trp.

In another preferred embodiment, the polypeptide is selected from the group consisting of:

(a) a polypeptide having the amino acid sequence of RNPRGEEGGPW (SEQ ID NO:2) and having 11-15 amino acids in length;

(b) a polypeptide which is derived from the polypeptide of (a) by substitution, deletion, or addition of 1-2 amino acids to the amino acid sequence of SEQ ID NO: 2 and which has the activity of inhibiting inflammation.

The present invention also provides dimer and polymer form of the compound of formula I, which exhibit the activity of inhibiting inflammation.

In the second aspect, the present invention provides an isolated nucleic acid molecule encoding the polypeptide according to the present invention.

In the third aspect, the present invention provides a pharmaceutical composition comprising:

(a) the polypeptide according to the present invention or a pharmaceutically acceptable salt thereof; and (b) a pharmaceutically acceptable carrier or excipient.

In another preferred embodiment, said composition is in the form of eyedrop, injection (such as periocular and intraocular injection), eye gel, or eye ointment.

In another preferred embodiment, said composition is in a slow-release dosage form.

In the fourth aspect, the present invention provides a use of the polypeptide or a pharmaceutically acceptable salt thereof according to the present invention for preparing medicaments for inhibiting inflammation or treating inflammation related diseases.

In another preferred embodiment, the inflammation related diseases is selected from the group consisting of ocular inflammatory diseases, pancreatitis, inflammatory bowel disease, lung inflammation, skin inflammation, rheumatoid arthritis, ankylosing spondylitis and so on.

In another preferred embodiment, the ocular inflammatory diseases comprises inflammatory diseases involved choroid, retina, conjunctiva, cornea or iris, including blepharitis, conjunctivitis, keratitis, scleritis, uveitis, retinal surrounding vein inflammation, optic neuritis and so on.

In the fifth aspect, the present invention provides a method for inhibiting inflammation in mammals, comprising the step of administering the polypeptide or a pharmaceutically acceptable salt thereof according to the present invention to a subject in need thereof.

In another preferred embodiment, the subject is human.

In another preferred embodiment, the inflammation is an inflammation associated with ocular inflammatory disease.

DESCRIPTION OF DRAWINGS

The following drawings are to illustrate the specific embodiments of the present invention. They should not be construed as limiting the scope of the present invention, which should be defined by the claims.

DETAILED DESCRIPTION OF THE INVENTION

Figure 1:
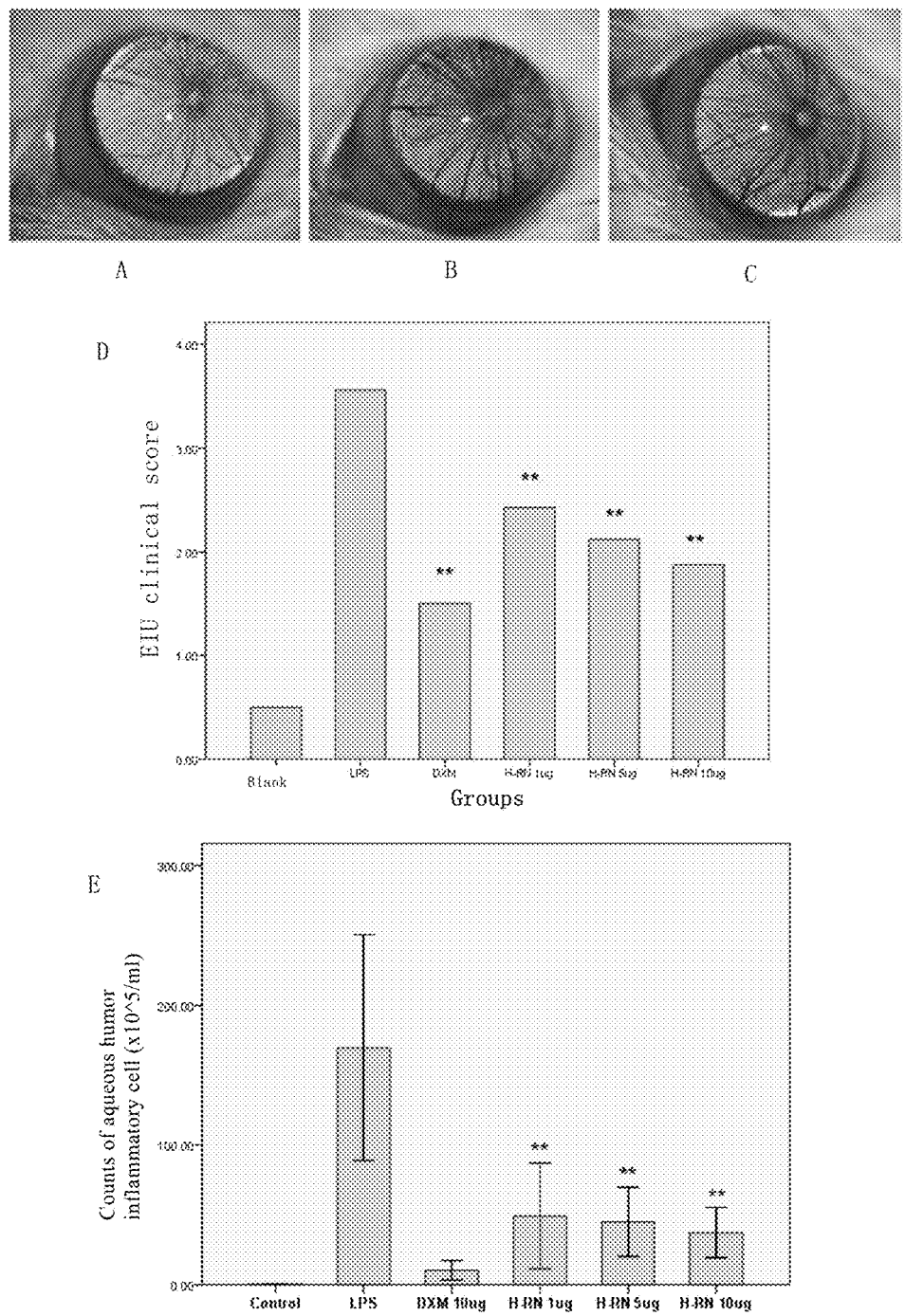
FIG. 1 shows the effect of H-RN polypeptide on inflammatory cellular infiltration of Rat Endotoxin-induced Uveitis (EIU) model. A. clinical manifestations of normal Wistar rats in the control group of intravitreal injection of PBS. B. clinical manifestations of the group of intravitreal injection of PBS induced with LPS. C. clinical manifestations of the group of intravitreal injection of H-RN (10 µg/µl) induced by LPS. D. EIU clinical score of control group, LPS group, DXM group and H-RN intervention group (1, 5, 10 µg/µl). E. counts of aqueous humor inflammatory cell of the control group, LPS group, DXM group and H-RN intervention group (1, 5, 10 µg/µl). n=9-15, ** $p<0.01$ vs LPS group.

After extensive and intensive studies, the inventors have firstly prepared a class of small molecular polypeptides exhibiting an activity of inhibiting inflammation with a molecular weight of only 1.254 kD. In particular, by utilizing the method of bioinformatics, the inventor designed several candidate sequences based on the homology analysis and analysis on the biological properties. Through solid-phase synthesis, and further screening through rat endotoxin-induced uveitis model, a novel class of small molecular polypeptides exhibiting the function of preventing and treating ocular inflammation was obtained, i.e. H-RN.

Due to the low molecular weight, the H-RN small peptides of the present invention can penetrate through various ocular tissue barriers and have good water solubility so that they can maintain a relatively high concentration in neutral tears, aqueous humor and vitreous humor. They are highly safe with a minor toxicity or side-effect to the biological tissue. The bioavailability in eye topical administration is high, thus the dose can be reduced, and hence the systemic toxicity can also be reduced. Based on the above work, the inventors finish the present invention.

Hepatocyte Growth Factor (HGF)

Hepatocyte growth factor (HGF) is a dimer composed of a heavy chain with a molecular weight of 69 kD and a light chain with a molecular weight of 34 kD through disulfide bond. The heavy chain has a hairpin structure at N-terminal, and four consecutive Kringle loop region close to its C-terminal. Genbank ID of HGF: AA64239.1.

HGF is a cytokine having a wide range of function, in addition to the function on liver cells, but also having a regulatory function on a variety of tissues and cells. Its main biological activity and physiological effects includes: starting liver regeneration, and promoting cell division, promoting cell motility, the role of tumor necrosis. The present inventors have screened a large number of fragments, and obtained fragments having the anti-inflammatory activity from HGF with a length of only 11 amino acids. The fragments have a small molecular weight, which is easy to penetrate through blood-ocular barrier, and has broad application prospects in the local anti-inflammatory of the eye.

LPS-Induced Inflammation Model in Mice

Lipopolysaccharides (LPS) are one kind of lymphocyte polyclonal stimulatory agents. LPS can directly activate B lymphocyte in vitro, thereby initiating a series of changes such as activation, proliferation and so on. After entering into the blood circulation, LPSs bind to mononuclear-phagocytic cells, endothelial cells through a variety of receptors (such as CD14, CD11/18 and scavenger lipoprotein receptors), stimulate non-specific immune function, and induce expression of cytokines and inflammatory mediators, such as pro-inflammatory cytokines TNF-α, IL-1, IL-6, IL-8, IFN γ and the like. Wherein TNF-α is a major rapid-response proinflammatory mediator, which is the most upstream media initiating proinflammatory cascade, and, to some extent, can reflect the changes of the disease.

Currently, LPS-induced mice model of inflammation can be widely used in screening and testing anti-inflammatory drugs with a stable and good representativeness.

Active Polypeptides

In the present invention, the terms "the polypeptide(s) of the present invention", "H-RN polypeptide(s)", "H-RN small peptide(s)", or "peptide(s) H-RN" are interchangeable and refer to a protein or polypeptide having peptide H-RN amino acid sequence (SEQ ID NO: 2) and exhibiting an activity of inhibiting inflammation. In addition, said terms comprise the variants of SEQ ID NO: 2 which exhibit the function of inhibiting inflammation. These variations include, but are not limited to, deletions, insertions and/or substitutions of 1-5 (typically 1-4, preferably 1-3, more preferably 1-2, most preferably 1) amino acids, and addition of one or more (typically less than 5, preferably less than 3, more preferably less than 2) amino acids at C-terminus and/or N-terminus. For example, a protein's functions are usually unchanged when an amino residue is substituted by another amino acid with similar or analogous properties in the art. For another example, generally, the structure and function of protein won't be changed by the addition of one or several amino acids at C-terminus and/or N-terminus.

The present invention further includes the active fragments, derivatives and analogs of H-RN protein. As used herein, the terms "fragments", "derivatives" and "analogs" refer to the polypeptides substantially maintaining the function or activity of inhibiting inflammation. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of H-RN polypeptide with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6His. According to the teachings herein, these fragments, derivatives and analogs are within the scope commonly known by the skilled person.

A class of preferred active derivatives is the polypeptides formed by replacing at most 5, preferably at most 3, more preferably at most 2, most preferably 1 amino acid in the amino acid sequence of formula I with amino acids having similar or analogous properties. These conservative variant polypeptides are preferably formed by carrying out the amino acid replacement according to Table I.

TABLE I

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides analogues of H-RN protein or polypeptide. These analogues can differ from naturally occurring H-RN polypeptide in amino acid sequence or in modifications that do not affect the sequence, or both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acelylation, or carboxylation. Also included is modification of glycosylation, e.g., the polypeptides produced through glycosylation modification during its synthesis and processing or in the further processing steps. These modifications can be conducted by exposing the polypeptide to glycosylation enzymes (e.g., mammalian glycosylation or deglycosylation enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salts derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals (such as sodium, potassium, calcium or magnesium), and esters, carbamate or other conventional "prodrug" forms.

Encoding Sequences

The present invention further relates to a polynucleotide encoding H-RN polypeptide. A preferred encoding sequence is (SEQ ID NO: 1)
CGAAATCCTCGAGGGGAAGAAGGGGGACCCTGG.

The polynucleotide of the present invention can be in a form of DNA or RNA. DNA can be the coding strand or the non-coding strand. The coding sequence encoding the mature polypeptide can be identical with the coding sequence indicated in SEQ ID NO: 1, or can be a degenerate variant thereof. As used herein, "degenerate variant" refers to a nucleic acid sequence which encodes the protein having the amino acid sequence of SEQ ID NO:2, but is different from the corresponding coding sequence in SEQ ID NO: 1.

The full length of H-RN nucleotide sequence or fragment thereof of the present invention can be obtained via PCR amplification, recombinant method or artificial synthesis. Currently, the DNA sequence encoding the polypeptide (or fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell engineered by using the vector or the coding sequence of the H-RN polypeptide of the present invention.

In another aspect, the present invention further comprises polyclonal antibodies or monoclonal antibodies specific to polypeptides encoded by H-RN DNA or fragments thereof, especially the monoclonal antibodies.

Preparation Method

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

One preferred method is to use liquid phase synthesis technique or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylfomamide for 20 minutes at room temperature to remove the Fmoc protective groups. Then the sequence is extended one by one from the C-terminus to the N-terminus according to the predetermined amino acid sequence. After synthesis, trifluoroacetic acid containing 4% p-methylphenol is used to cleave the peptide from the resin and the protective groups are removed. The resin can be filtered off, and the crude peptide can be obtained via precipitation with ether. The solution of the resultant product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine (DIEA)/dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular sieve Sephadex G10 or Tsk-40f. Then the desired peptide is obtained via high pressure liquid purification. Various coupling agents and coupling methods known in the peptide chemistry can be used to couple each amino acid residue. For example, dicyclohexylcarbodiimide (DCC), hydroxylbenzotriazole (HOBt) or 1,1,3,3-tetramethyluronium Hexafluorophosphate (HBTU) can be used for direct coupling. The purity and structure of the resultant short peptide can be verified by reverse phase HPLC and mass spectrometry.

In a preferred embodiment, the polypeptide H-RN of the present invention is prepared by solid phase method according to its sequence, and purified by high performance liquid chromatography, thereby obtaining freeze-dried powder of target peptide with high purity. The powder is stored at −20° C.

Another method is to produce the polypeptide of the present invention by a recombinant technique. With the conventional recombinant DNA technique, the polynucleotide of the present invention can be used to express or produce recombinant H-RN polypeptides. Generally, the method comprises the following steps:

(1) Transforming or transducing a suitable host cell with a polynucleotide or variant thereof encoding the H-RN polypeptide of the present invention or a recombinant expression vector containing said polynucleotide;

(2) Culturing the host cell in a suitable culture medium;

(3) Isolating and purifying protein from the culture medium or cells.

The recombinant polypeptide may be expressed in the cells, or expressed on the cell membrane, or secreted out of the cell. If desired, the recombinant protein can be isolated and purified according to the physical, chemical and other properties thereof by various isolation methods. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and combinations thereof.

It is also contemplated to link multiple polypeptides of the present invention in series due to their short length. After recombinant expression, the expressed product is obtained and enzyme-cleaved to form the desired small peptides.

Pharmaceutical Composition and Methods of Administration

In another aspect, the present invention further provides a pharmaceutical composition, comprising (a) a safe and effective amount of the polypeptide of the present invention or a pharmaceutically acceptable salt thereof; and (b) a pharmaceutically acceptable carrier or excipient. The amount of the polypeptide of the present invention generally is 10 µg to 100 mg per dose, preferably 100-1000 µg per dose.

For the purpose of the invention, the effective dose is about 0.01 mg to 50 mg of the polypeptide of the present invention per kg body weight, preferably 0.05 mg to 10 mg of the polypeptide of the present invention per kg body weight administered to an individual. Further, the polypeptide of the present invention can be used alone, or in combination with other therapeutic agents (for example, formulated into a pharmaceutical composition comprises corticosteroids, immunosuppressants or non-steroidal anti-inflammatory drugs, etc.).

The pharmaceutical composition can further comprise a pharmaceutically acceptable carrier. The term "pharmaceutically acceptable carrier" refers to the carrier for using in administering the therapeutic agents. The term refers to such drug carriers that themselves do not induce antibody deleterious to the subject receiving the composition, and do not produce excessive toxicity upon administration. These carriers are well known by the skilled person in the art. The detailed discussion about pharmaceutically acceptable excipients can be found in Remington's Pharmaceutical Sciences (Mack Pub. Co., N.J., 1991). Such carriers include, but are not limited to, saline, buffer solution, glucose, water, glycerin, ethanol, adjuvant or combinations thereof.

The pharmaceutically acceptable carrier in the therapeutic composition can comprise liquid, such as water, saline, glycerin, and ethanol. Moreover, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulating the composition of the present invention, it can be administered via conventional routes which include, but are not limited to, administering intra-ocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include eyedrop, injection, ophthalmic gel, and eye ointment.

The pharmaceutical composition can be formulated by mixing, diluting or dissolving according to the conventional methods. And, occasionally, suitable medicine additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulation can be carried out in a conventional manner according to the dosage form.

For example, formulation of eyedrop can be prepared as follows: dissolving polypeptide H-RN or a pharmaceutically acceptable salt thereof and the basic substances in sterile water by heating (surfactant is dissolved in said water), adding polyvinyl pyrrolidine, optionally adding suitable medicine additives, such as preservatives, stabilizing agents, buffering agents, isotonicities, anti-oxidants and tackifiers, and then allowing them completely dissolved.

The pharmaceutical composition of the present invention can further be administered in a form of slow release formulation. For example, the polypeptide H-RN or a salt thereof can be incorporated into a pill or microcapsule in which a slow release polymer is used as carrier, and then the pill or microcapsule is implanted into the tissue to be treated by operation. Furthermore, the polypeptide H-RN or a salt thereof can be used by insertion of intra-ocular lens pre-coated with said drugs. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc., Preferable examples of the slow release polymer include the biodegradable polymers, such as polymer of lactic acid, and lactic acid-glycolic acid copolymer.

When the pharmaceutical composition of the present invention is used in the actual treatment, the dose of the polypeptide H-RN or a pharmaceutically acceptable salt thereof, as an active ingredient, can be suitably determined according to the body weight, age, gender, symptom of each patient. For example, when topically dropping in the eye, the concentration of the active ingredient generally is 0.1-10 wt %, preferably 1-5 wt %, 2-6 times per day and 1-5 drops for each time.

Indications

Polypeptides of the present invention and derivatives thereof are useful for preparing medicaments for inhibiting inflammation or treating inflammation-related diseases.

As used herein, the term "inflammation" includes infectious inflammation and non-infectious inflammation. During the inflammatory response, pro-inflammatory cytokines involve in the occurrence and development of inflammation. Wherein, TNF-α is the earliest appearing and most important inflammatory mediator in the process of inflammation, and can activate neutrophils and lymphocytes, increase permeability of the endothelial cells, regulate metabolic activities of other tissues and promote synthesis and release of other cytokines.

Inflammation-Related Diseases

Inflammation-related diseases of the present invention comprises ocular inflammatory disease, pancreatitis, inflammatory bowel disease, lung inflammation, skin inflammation, rheumatoid arthritis, ankylosing spondylitis.

Ocular Inflammatory Diseases

The ocular inflammatory diseases of the present invention comprises various ocular inflammatory diseases involved choroid, retina, conjunctiva, cornea or iris, including blepharitis, conjunctivitis, keratitis, scleritis, uveitis, retinal surrounding vein inflammation, optic neuritis and so on.

In the present invention, all of the inflammation-related diseases, particularly ocular inflammatory diseases, are characterized in the increase of TNF-α. Therefore, the polypeptide of the present invention can inhibit inflammation or treat inflammation-related diseases, as long as the polypeptide can effectively inhibit the pro-inflammatory cytokines TNF-α.

INDUSTRIAL APPLICABILITY

The pharmaceutical composition containing the peptide or a pharmaceutically acceptable salt thereof of the present invention as an active ingredient exhibits significant inhibition activity on inflammation. As verified by in vivo, in vitro tests, the polypeptides of the present invention can not only inhibit the endotoxin-induced uveitis in rats, but also inhibit the expression of proinflammatory cytokines in LPS-induced RAW264.7 cells without significant side effects on the RAW264.7 cells.

The Main Advantages of the Present Invention Include:

(a) The polypeptide of the present invention has low molecular weight, so that it can penetrate various of ocular tissue barriers.

(b) The polypeptide of the present invention has good water solubility, so that it can maintain relatively high concentration in neutral tears, aqueous humor and vitreous humor.

(c) The polypeptide of the present invention has high safety with less toxicity to the tissue of the organism.

(d) The polypeptide of the present invention can be prepared via solid phase synthesis with high purity, high yield and low cost.

Therefore, the polypeptide of the present invention can be developed into a medicine for treating inflammatory ophthalmopathy and related inflammatory diseases, such as inflammatory bowel disease, skin inflammation, etc.

The invention is further illustrated by the following examples. These examples are only intended to illustrate the invention, but not to limit the scope of the invention.

For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Synthesis of Polypeptide

H-RN polypeptide (SEQ ID NO: 2) was synthesized by using the commercially available SYMPHONY polypeptide synthesizer. The steps are listed as follows:

1. The desired protective solution for amino acids, condensation reagents, and cleavage reagents were calculated and prepared according to the software, and sufficient amount of DMF, DCM were added into the corresponding flasks in the synthesizer.

2. 100 μmol of FMOC-Ala-Wang-Resin was added into the reactor.

3. A 15 ml centrifuge tube was placed to the tunnel for collecting cleavage fluid.

4. The program was set as follows: typically, 30 mins for resin swelling, 5 mins and 15 mins for deprotection respectively, 30 mins for condensation, and 2 hrs for cleavage program.

5. The synthesis was conducted as programmed.

6. Finally, the cleavage fluid was precipitated by ether, centrifuged, blow-dried and purified by HPLC.

120 mg of polypeptide H-RN was obtained as white powder with good water solubility, purity >95% and then sealed and stored for use at −20° C.

Example 2

Effects of H-RN on inflammatory cell infiltration of EIU model

1. Materials and methods:

1.1 Experiment animals and materials: healthy male Wistar rats, 140-180 g, 8-10 weeks old, were purchased from Animal Center of Chinese Academy of Medical Sciences; Lipopolysaccharides (LPS), derived from *Escherichia coli*, was purchased from SIGMA-Aldrich Corporation (U.S.A).

1.2 Model establishment and Intervention test: Wistar rats were randomly divided into six groups (9-15 rats for each group) which were LPS group, LPS+1 μg/μl H-RN intervention group, LPS+5 μg/μl H-RN group, LPS+10 μg/μl H-RN group, LPS+10 μg/μl DXM and normal control group (PBS) respectively. 200 μg LPS (2 mg/ml, 100 μl, dissolved in sterile saline) was subcutaneously injected into right foot pad of rats, thereby establishing EIU model. The normal control group was subcutaneously injected with 100 μl sterile saline into the right foot pad of rats. In LPS group, LPS+H-RN (1, 5, 10 μg/μl) intervention group and LPS+10 μg/μl DXM group, each rat was subcutaneously injected with 200 μg LPS into the right foot pad, meanwhile, PBS 10 μl, H-RN PBS solution (1, 5 and 10 μg/μl) 10 μl and DXM PBS solution (10 μg/μl) 10 μl were injected into vitreous chamber respectively.

1.3 Qualitative observation for Clinical manifestations of EIU rats: 24 hours after drug and LPS intervention, rats were observed by biological microscope. The clinical manifestations of rats were evaluated and scored by an independent observer according to the method of Behar-Cohen et al. The severity of EIU was represented by 0-4 scores: 0: no inflammation; 1: mild dilation in conjunctiva and iris vessel; 2: moderate dilation in conjunctiva and iris vessel with anterior chamber flare; 3: severe iris hyperemia with severe anterior chamber flare; 4: anterior chamber cellulose-like exudation, posterior synechia, miosis and hypopyon in addition to 3 points.

1.4 Quantitative count for inflammatory cell infiltration in rat aqueous humor: 24 hours after LPS and drug intervention, rats were sacrificed in excess of anesthesia. Under an operating microscope, aqueous humor (30-40 μl/binoculus) was collected by anterior chamber paracentesis with a 30-gauge microsyringe at 1 mm from rat corneal limbus. Aqueous humor samples were diluted with an equal amount of trypan blue dye liquid. Cells in aqueous humor were counted using a hemocytometer under light microscopy by two independent technicians for each region (equivalent with 0.1 μl). The average of the four regions was the number of cells contained in 1 μl aqueous humor.

1.5 Statistic Analysis

The experiment data was shown as $\bar{x}\pm s$. A one-way ANOVA was used to compare the change of inflammatory cell infiltration of rats in each group. $P<0.05$ represents statistical significance.

2. Results 2.1 Qualitative observation for clinical manifestations of EIU rats: Rats in normal control group had no significant inflammation, and EIU clinical score was 0.50±0.54; 24 hours after LPS injection, rats in LPS group showed inflammation manifestations, such as dilatation and tortuosity of the iris vascular, anterior chamber flare, membranous substance in pupillary area, occlusion of pupil etc. and EIU clinical score was 3.56±0.51. Compared with LPS group, the inflammation manifestations of H-RN (1, 5, 10 μg/μl) intervention group were significantly reduced and only light to moderate iris vessel hyperemia was observed without exudation. And EIU clinical scores were 2.42±0.53, 2.12±0.64 and 1.92±0.27 ($P<0.01$) (FIG. 1A, 1B, 1C, 1D).

2.2 Quantitative count for inflammatory cell infiltration in rat aqueous humor: in aqueous humor of rats in normal control group, there was no significant inflammatory cell infiltration; in aqueous humor of rats in LPS group, the count of inflammatory cells was $164.20\pm142.7\times10^5$ cells/ml, which was, compared with the control group, significantly increased ($P<0.01$); and compared with LPS group ($P<0.01$), the counts of inflammatory cells in 1, 5, 10 μg/μl H-RN intervention group was significantly decreased, which were $49.14\pm40.84\times10^5$, $40.40\pm31.34\times10^5$ and $37.35\pm21.44\times10^5$ cells/ml respectively ($P<0.01$, respectively) (FIG. 1E).

3. Summary

By establishing the endotoxin-induced uveitis model in rats, H-RN was demonstrated having the effect of inhibiting inflammatory cell infiltration through the clinical manifestation observation and scoring, aqueous humor inflammatory cells counting, etc., thereby reducing inflammation reaction and relieving clinical symptoms.

Example 3

Effect of H-RN on LPS-Induced Proinflammatory Cytokine in RAW264.7 Cells

1. Materials and Methods 1.1 Experimental cell strain and Materials: murine peritoneal macrophage cell strain RAW264.7 were purchased from the Cell Bank of Shanghai Institutes for Biological Sciences, CAS; DMEM high glucose medium was purchased from GIBCO; mouse tumor necrosis factor-α (TNF-α) and interleukin-6 (IL-6) enzyme-linked immunosorbent assay (ELISA) kits were purchased from R & D company, US.

1.2 Model establishment and Intervention test: RAW264.7 cells were cultured in high glucose DMEM medium containing 10% fetal bovine serum (FBS), and 100 U/ml double antibiotics of penicillin and streptomycin, and placed in 37° C., 5% $CO_2$ incubator for amplification. Cells at Logarithmic growth phase were seeded in 24-well plates at $2.5 \times 10^5$/ml. When adhered cells grew well and were cultured to 80-90% of confluence, the medium was replaced by a DMEM medium without 10% FBS for serum-starved culture for 24 hours. RAW264.7 cells were randomly divided into control group, LPS group, LPS+H-RN group with sextuplicate wells for each group. LPS group and LPS+H-RN group were added with 500 µl of different concentrations of H-RN (1, 10, 100 µM) and LPS (100 ng/ml) and the control group was added with an equal volume of DMEM medium, each group was placed in 37° C., 5% $CO_2$ incubator and routinely cultured. Cell supernatants were collected after 24 hours.

1.3. Statistic Analysis

The experiment data was shown as $\bar{x} \pm s$. SPSS 11.0 statistical package was used for statistic analysis and one-way ANOVA was used to compare TNF-α and IL-6 level in supernatant between the groups, and $P<0.05$ represents statistical significance.

Figure 2:
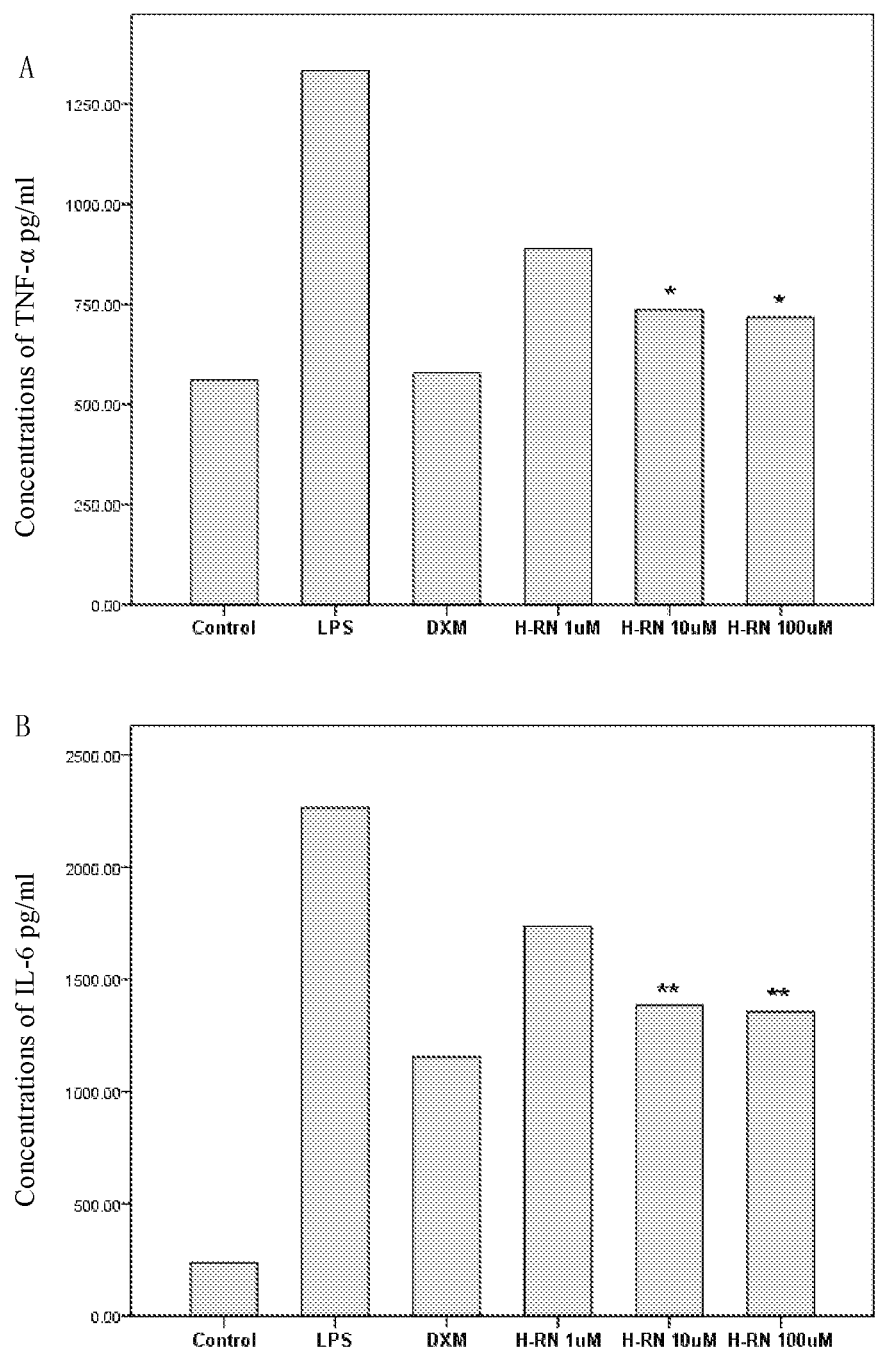
FIG. 2 shows the effect of H-RN polypeptide on expression of proinflammatory cytokines in RAW264.7 cells induced by LPS. A. measured concentrations of TNF-α in RAW264.7 cell supernatant of normal control group, LPS group and H-RN intervention group (1, 10, 100 µM). B. measured concentrations of IL-6 in RAW264.7 cell supernatant of normal control group, LPS group and H-RN intervention group (1, 10, 100 µM). n=10,* $p<0.05$,** $p<0.01$ vs LPS group.

2. Results 2.1 Determination of TNF-α concentration: in cell supernatant of LPS group, the concentration of TNF-α (1333.00±476.59 pg/ml) was significantly higher than that of the control group (561.00±25.65 pg/ml). H-RN intervention (10, 100 µM) inhibited expression levels of TNF-α in cell supernatant which were 737.00±155.56 pg/ml and 718.00±79.19 pg/ml respectively. Compared with the LPS group, the difference was statistically significant ($P<0.05$). However, 1 µM H-RN intervention group and LPS group showed no significant difference ($P>0.05$) (FIG. 2A).

2.2 Determination of IL-6 concentration: in cell supernatant of LPS group, the concentration of IL-6 (2650.00±106.07 pg/ml) was significantly higher than that of the control group (213.00±15.56 pg/ml), and H-RN intervention (10, 100 µM) significantly inhibited the expression levels of IL-6 in cell supernatant which were 1385.00±101.54 pg/ml and 1355.00±134.35 pg/ml respectively. Compared with the LPS group, the difference was statistically significant ($P<0.01$). However, 1 µM H-RN intervention group and LPS group showed no significant difference ($P>0.05$) (FIG. 2B).

3. Summary

Macrophages play an important role in the body's immune system. In this experiment, a cell model of inflammation was established through stimulating mouse peritoneal macrophage cell strain RAW264.7 using LPS. Different concentrations of H-RN polypeptides were used for intervention, and the concentrations of inflammatory cytokines TNF-α and IL-6 in cell supernatant were analyzed, thereby confirming that H-RN could inhibit the expression of inflammatory cytokines.

Example 4

Cell Safety Test for H-RN

1. Experimental Methods 1.1 Experimental cell strain and Materials: murine peritoneal macrophage cell line RAW264.7 were purchased from the Cell Bank of Shanghai Institutes for Biological Sciences, CAS; DMEM high glucose medium were purchased from GIBCO; MTS were purchased from Promega, prepared into 300 mmol/L in PBS (pH 6.0) and stored at −20° C. in darkness.

1.2 Model establishment and Intervention test: RAW264.7 cells were cultured in high glucose DMEM medium containing 10% fetal bovine serum (FBS), and 100 U/ml double antibiotics of penicillin and streptomycin, and placed in 37° C., 5% $CO_2$ incubator for amplification. Cells at logarithmic growth phase were seeded in 96-well plates at $1 \times 10^5$/ml. When adhered cells grew well and were cultured to 80-90% of confluence, the medium was replaced by a DMEM medium without 10% FBS for serum-starved culture for 24 hours.

1.3 Cytotoxicity assay (MTS colorimetric method): After the cells were cultured for 24 hours in serum starvation, different concentrations of H-RN (0.1, 1, 10 µM, 100 µM, 1 mM, 100 µl) were added into each well with sextuplicate wells for each concentration. The blank control group was added with an equal volume of DMEM medium. The plates were placed in 37° C., 5% $CO_2$ incubator and cultured for 24 hours, added with 20 µl of MTS solution to each well and cultured for another 4 hours. The absorbance of each well was measured by an enzyme-linked immunosorbent detector in 490 nm, and the relative growth rate (RGR) of cells was calculated. Formula: RGR=A value of experimental group/A value of control group×100%.

1.5. Statistic analysis: The experiment data was shown as $\bar{x} \pm s$. SPSS 11.0 statistical package was used for statistic analysis and one-way ANOVA was used to compare RGR of cells between the groups, and $P<0.05$ represents statistical significance.

Figure 3:
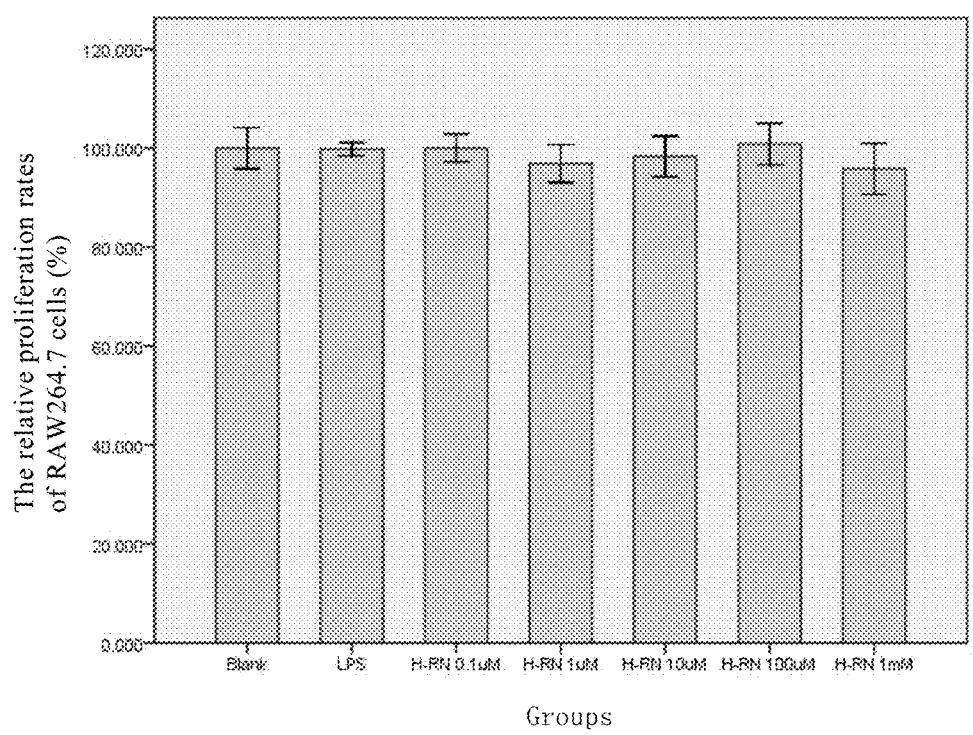
FIG. 3 shows the relative proliferation rates of RAW264.7 cells under different concentrations of H-RN (0.1, 1, 10, 100 µM, 1 mM) intervention. n=6.

2. Results: RGR of cells in blank, LPS and various concentrations group were 100.05±3.95%, 99.79±1.28%, 96.87±3.64%, 100.06±2.67%, 98.29±3.91%, 100.80±4.00% and 95.83±4.92%. Compared with the blank group, RGRs of cells treated with different concentrations of H-RN (0.1, 1, 10 µM, 100 µM, 1 mM) exhibited no significant difference ($P>0.05$) (FIG. 3).

3. Summary: H-RN within a concentration range of 0.1 µm-1 mM had no significant toxic effects on cells proved by detecting the effect of different concentrations of H-RN on RGR. The concentration of the drug used in the experiment (1-100 µM) was within safe limits.

Example 5

Preparation of Derived Polypeptides and Test of Inhibiting the Inflammatory Reaction Following derived polypeptides were prepared according to the method in example 1. And the inhibiting effects of the polypeptides (1 μM, 10 μM, 100 μM) derived from H-RN on the inflammatory cytokines TNF-α and IL-6 were determined according to Example 3. Wherein, when the concentration of the polypeptide was 10 μM, the results are shown in table 2:

TABLE 2

| Samples (10 μM) | Sequence | SEQ ID NO. | TNF-α (pg/ml) | IL-6 (pg/ml) |
|---|---|---|---|---|
| Derived polypeptide 1 (H-RN-1) | RNPKGEEGGPW | 3 | 724.98 | 1365.29 |
| Derived polypeptide 2 (H-RN-2) | KQPRGEEGGPW | 4 | 701.63 | 1356.46 |
| Derived polypeptide 3 (H-RN-3) | RNPRPEEGGAY | 5 | 792.31 | 1402.54 |
| Derived polypeptide 4 (H-RN-4) | QNPRGDEPGPW | 6 | 765.92 | 1411.87 |
| Derived polypeptide 5 (H-RN-5) | NPRGEEGGP | 7 | 745.70 | 1395.34 |
| Derived polypeptide 6 (H-RN-6) | RNPRGEEGGPWCF | 8 | 696.77 | 1369.41 |
| Control (LPS) | | | 1425.60 | 2713.95 |

The results showed that TNF-α and IL-6 were significantly inhibited when the concentration of the H-RN derived polypeptide in treatment groups reached 10 μM. Thus, the polypeptides and derivatives thereof of the present invention could effectively inhibit inflammation reaction.

Example 6

Effect of H-GP Hybrid Peptide Molecules on Inflammatory Cell Infiltration of EIU Model and Proinflammatory Cytokines in LPS-Induced RAW264.7 Cells The sequence of H-GP hybrid peptide molecules was shown in SEQ ID NO.: 9: GPERWRGPNGE 6.1 Effect of H-GP on inflammatory cell infiltration was tested using the EIU model in Example 2

6.1.1 Qualitative observation of Clinical manifestations of EIU rats:

EIU score of LPS+10 μg/μl H-GP group was 3.32±0.61, and P>0.05, compared with LPS group.

6.1.2 Quantitative count of inflammatory cell infiltration in aqueous humor of rat:

The count of inflammatory cells in aqueous humor of rat of LPS+10 μg/μl H-GP group was 134.66±98.23×$10^5$ cells/ml, P>0.05, compared with LPS group.

6.2 The method of Example 3 was used to test the effect of H-GP on proinflammatory cytokines in LPS-induced RAW264.7 cells The concentration of TNF-α and IL-6 in cell supernatant of 100 μM H-GP group, compared with that of LPS group, showed no significant difference (p>0.05).

Thus, the hybrid peptide H-GP had no inhibitory effect on cell infiltration or pro-inflammatory cytokines.

Example 7

Preparation of Eyedrop

The following components were mixed via conventional techniques to obtain an injection, the formulation of which was as follows:

| | |
|---|---|
| H-RN peptide | 10 mg |
| Hydroxylpropyl methyl cellulose | 0.03 g |
| Sterile water | q.s. to 10 ml |
| Osmotic pressure | 300 Osm |
| pH | 6.8-7.1 |

Three volunteers of moderate acute uveitis used the eyedrop for one week, 4 times per day (or one time every 2 hours), and 2 drop/eye for each time.

Wherein, grading criteria of acute uveitis are listed as follows:

① mild: ciliary congestion, KP +~++, anterior chamber inflammatory cells 0 ~++, anterior chamber flare 0 ~++. ② Moderate: ciliary congestion, KP ++~+++, anterior chamber inflammatory cells ++~+++, anterior chamber flare ++~+++. ③ severe: Mixed congestion, KP +++~++++, anterior chamber inflammatory cells +++~++++, anterior chamber flare +++~++++, a anterior chamber cellulose-like exudation, hypopyon.

Criteria for therapeutic effect are listed as follows:

The main evaluation indexes were vision situation, eye symptoms, anterior chamber inflammatory cells, and aqueous flare. Therapeutic effect was divided into four grades: cured, markedly effective, effective and ineffective and were scored respectively.

Cured: ① visual acuity recovered to 1.0 or more; ② self-consciousness of disappearance of eye symptoms; ③ anterior chamber inflammatory cells (−), aqueous flare (−).

Markedly effective: ① visual acuity improved by 4 lines or more; ② self-consciousness of decrease in eye symptoms; ③ decrease in anterior chamber inflammatory cells, ++++→++/+++→+, weakened aqueous flare, ++++→++/+++→+.

Effective: ① visual acuity improved by 2 lines or more; ② self-consciousness of decrease in eye symptoms; ③ decrease in anterior chamber inflammatory cells, ++++→+++/+++→++, weakened aqueous flare, ++++→+++/+++→++.

Ineffective: ① no increase in visual acuity; ② no self-consciousness of improvement in eye symptoms; ③ no decrease or increase in anterior chamber inflammatory cells, and aqueous flare unchanged.

Results: After a week of treatment (2 times a day, 2 drops/eye for each time), visual acuity of three patients increased by 2 lines or more, and there were self-consciousness of improvement in eye symptoms, decrease in keratic precipitates, and decrease in anterior chamber flare and cells. The results show that the eye drops could inhibit ocular inflammation.

Discussion

H-RN polypeptides of the invention has a significant effect in inhibiting inflammation, which is reflected in: H-RN can inhibit the inflammatory cell infiltration of endotoxin-induced uveitis model of rat; H-RN can inhibit the expression of pro-inflammatory cytokines in LPS-induced RAW264.7 cell; H-RN have no significant cytotoxicity within a certain range of concentrations (0.1 μM-1 mM). In summary, H-RN polypeptide has broad application prospects in suppressing inflammation.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

The invention claimed is:

1. A method for treating an ocular inflammatory disease, comprising administering a polypeptide or a pharmaceutically acceptable salt thereof at a concentration of at least 10 μM, to a subject having an ocular inflammatory disease, wherein the polypeptide is selected from the group consisting of peptide SEQ ID NOS: 2-8, wherein the polypeptide exhibits an activity of inhibiting inflammation, and wherein the ocular inflammatory disease is selected from the group consisting of blepharitis, conjunctivitis, scleritis, and optic neuritis.

2. The method of claim 1, wherein the polypeptide is one or more polypeptides selected from the group consisting of: SEQ ID NO.3, SEQ ID NO.4, SEQ ID NO.5, SEQ ID NO.6, SEQ ID NO.7, and SEQ ID NO.8.

3. The method of claim 1, wherein the polypeptide is administered as a pharmaceutical composition comprising:
   (a) the polypeptide or a pharmaceutically acceptable salt thereof; and
   (b) a pharmaceutically acceptable carrier or excipient.

4. The method of claim 3, wherein the pharmaceutical composition is in a dosage form of eyedrop, injection, eye gel, or eye ointment.

5. The method of claim 3, wherein the pharmaceutical composition further comprises a corticosteroid, an immunosuppressant, or a non-steroidal anti-inflammatory drug.

* * * * *